United States Patent [19]

Stadler et al.

[11] Patent Number: 5,714,590
[45] Date of Patent: Feb. 3, 1998

[54] PROCESS FOR RECOVERING A HIGH-PURITY VIRUS-INACTIVATED FACTOR VIII BY ANION EXCHANGER CHROMATOGRAPHY

[75] Inventors: Monika Stadler, Schwechat, Austria; Horst Schwinn, Marburg, Germany

[73] Assignee: Octapharma A.G., Ziegelbrucke, Switzerland

[21] Appl. No.: 284,403

[22] PCT Filed: Jan. 20, 1993

[86] PCT No.: PCT/EP93/00114

§ 371 Date: Aug. 29, 1994

§ 102(e) Date: Aug. 29, 1994

[87] PCT Pub. No.: WO93/15105

PCT Pub. Date: Aug. 5, 1993

[30] Foreign Application Priority Data

Feb. 1, 1992 [DE] Germany ............... 42 04 694.7

[51] Int. Cl.⁶ ............... C07K 1/18; C07K 14/755; A61K 38/37
[52] U.S. Cl. ............... 530/416; 530/383; 514/12
[58] Field of Search ............... 530/380, 383, 530/416, 829, 830; 514/12, 21

[56] References Cited

U.S. PATENT DOCUMENTS

4,876,241  10/1989  Feldman et al. ............... 514/2

FOREIGN PATENT DOCUMENTS

| 3233189 | 12/1991 | Australia. |
|---|---|---|
| 0337144 | 10/1989 | European Pat. Off.. |
| 0359593 | 3/1990 | European Pat. Off.. |
| 0367840 | 5/1990 | European Pat. Off.. |
| 0 416 983 | 8/1990 | European Pat. Off.. |

*Primary Examiner*—Nancy Degen
*Attorney, Agent, or Firm*—Jacobson, Price, Holman & Stern, PLLC

[57] ABSTRACT

Described is an economical process for the recovery of factor VIII from blood plasma or cryoprecipitate. In the process, anion exchanger chromatography is conducted using a separating material based on carriers containing hydroxyl groups, the surfaces of which carriers have been coated with covalently boded polymers. The polymers contain repeating units represented by formula (I).

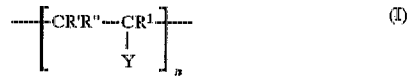

4 Claims, No Drawings

PROCESS FOR RECOVERING A HIGH-PURITY VIRUS-INACTIVATED FACTOR VIII BY ANION EXCHANGER CHROMATOGRAPHY

The present invention relates to a process for recovering a highly pure virus-inactivated factor VIII from blood plasma or cryoprecipitate by means of anion exchanger chromatography.

In EP-A-0 238 701 there has been described a process for the production of a high-purity non-infectious antihemophilia factor, wherein fibrinogen, globulins, albumins and other interfering components are removed from the cryoprecipitate by means of an ethanol precipitation. The accumulation from the cryoprecipitate is necessary because the factor VIII is contained in the material only in very low amounts. However, this accumulation step impairs the AHF content in the final product. The processes hitherto known for the production of factor VIII do only produce very low amounts of active substance. Thus, by the application of the factor VIII produced via the conventional route, the patient will be burdened with large amounts of antigenic substances. This procedure is not without risk. Therefore, there have been plenty of attempts for further accumulating the factor VIII by separation operations. Thus, it has been attempted to obtain products having a higher specific activity by means of affinity chromatography using animal antibodies directed against factor VIII. However, this technique is very expensive and cost-intensive. On the other hand, this technique is also not quite unobjectionable, because also a certain amount of animal protein is always eluted from the column in each chromatographic separation.

European Patent Application No. 88 108 458.6 describes a process for producing a highly pure virus-free antihemophilia factor wherein a cryoprecipitate comprising factor VIII is treated with aluminum hydroxide and with biologically compatible organic solvents/detergents, in a preferred embodiment followed by further gel permeation chromatography using ion exchanger material. European Patent Application No. 88 118 478.2 describes a chromatography material based on copolymers of oligoethyleneglycols, glycidyl methacrylates and pentaerythritol dimethacrylates as being particularly suitable for producing a highly pure virus-free factor VIII.

WO 90/14886 describes a medium for separating proteins. The material disclosed therein describes a water-insoluble matrix bearing a plurality of polyamine moieties, said polyamine moieties comprising at least 3 basic nitrogen atoms, and said nitrogen atoms being separated by a chain of at least two carbon atoms positioned therebetween, with at least 5 of such carbon atoms being present in the case that each polyamine group has a total of 3 nitrogen atoms. This separating medium is suitable for at least a partial purification of factor VIII.

EP 0 343 275 A1 relates to a process for producing a highly pure antihemophilia factor (AHF or factor VIII) which, in purifying a cryoprecipitate, has been rendered virus-free by a treatment with biologically compatible organic solvents/detergents. The process is characterized in that the cryoprecipitate, prior to the removal of viruses therefrom, is thawed, is extracted with water containing from 1 to 3 U/ml of heparin at pH 6.5–7.5, is then admixed with an aluminum hydroxide suspension and, after cooling to from 10° C. to 18° C. and adjusting the pH value to from 6 to 7, is subjected to centrifugation and filtration and then further processed in a per se known manner. It is particularly advantageous that the sample, after the removal of the virusses, is subjected to gel permation chromatography on ion exchanger materials.

It is true, the process described in European Patent Application No. 88 108 458.6 provides an increase in the yield of factor VIII; however, the yield of the biologically active factor VIII still is not optimal.

Therefore, the technical problem defining the object of the invention is to provide a process which is capable of improving the recovery of a biologically active factor VIII from the sources of cyroprecipitate or blood plasma and ensures a more economical procedure.

This problem surprisingly is solved by a process according to the features of claim 1. The subclaims relate to preferred embodiments of the process according to the invention.

The separating materials to be used according to the invention consist of carrier particles as disclosed in EP-A-0 337 144. These are carrier particles having hydroxyl groups onto which a polymeric material has been grafted via the carbon atoms in the α-positions relative to the hydroxyl groups. The carrier materials may include any of the generally known porous and non-porous chromatography supports having primary or secondary aliphatic hydroxyl functions present on the surfaces thereof. Among these preferred are hydrophilic polymers based on acrylates and/or methacrylates, polyvinylalcohol-based polymers, diol-substituted silicagels, agarose-based polysaccharides, cellulose, celluose derivatives or dextran-based polymers. Other polymers or copolymers based on monomers such as vinyl compounds, acrylamide, (meth)acrylic acid esters or (meth)acrylonitrile in hydroxylated form may of course be employed as well.

The polymeric material of the formula I according to claim 1 bound to the carrier particles through the carbon atoms in the α-positions relative to the hydroxyl groups is derived from monomers represented by the formulae II and/or III, wherein the substituents are as defined hereinbelow.

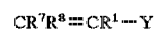

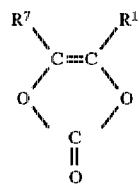

These monomers represent (meth)acrylic acid ($Y=$—COOH), (meth)-acrylic acid derivatives

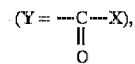

allyl amines ($Y=$—$CH_2NH_2$, —$CH_2NR^2R^3$), (meth) acrylonitriles ($Y=$—CN), acroleins ($Y=$—CHO), vinyl carboxylates ($Y=$—$OCOCHR^5R^6$) or vinylene carbonates of the formula III.

All of these monomers are substances that are polymerizable in an aqueous solution via a free radical initiated polymerization and have reversibly bonding groups which may be neutral, acidic or basic.

If vinylene carbonates of the formula III or vinyl carboxylates $CR^7R^8=CR^1$—$OCOCHR^5R^6$ of the formula II are employed, then it is preferred that the resulting product is converted into a separating material having hydroxyl groups. This conversion into a hydroxyl phase is effected by means of a per se known mild alkaline or acidic saponification. For example, the reaction may be carried out with a methanol solution of $K_2CO_3$ at room temperature as described, for example, by Y. Tezuka et al., in Macromol. Chem. 186, 685–694 (1985).

$R^1$ in the formulae I (cf. claim 1), II and III preferably represents hydrogen, i.e. the acrylic acid derivatives are preferred.

Y in formula II preferably represents

—$OCOCHR^5R^6$ or —$CH_2NH_2$; preferred in the second place, are —CN or —CHO. Accordingly Y in formula I in the first place represents

—OH (since preferably the moiety —$OCOCHR^5R^6$ is converted into a hydroxyl phase) or —$CH_2NH_2$, and as second preference —CN or —CHO.

$R^5$ and $R^6$ independently represent H or an alkyl group having up to 5 carbon atoms. It is preferred that at least one of the groups $R^5$ and $R^6$ is H. The following moieties are particularly preferred: Acetyloxy-, propionyloxy-, butyryloxy-, valeryloxy- and hexanoyloxy-groups.

X in formula I as well as in formula II represents —$OR^4$, —OH or —$NR^2R^3$ and preferably —$NR^2R^3$.

Preferred are compounds in which X represents —$NR^2R^3$ and one of $R^2$ and $R^3$ is H.

The moieties $R^2$ and/or $R^3$ preferably represent an alkyl, phenyl, phenylalkyl or alkylphenyl group, where the alkyl and/or phenyl groups may be mono- or poly-substituted preferably mono- or disubstituted and particularly preferred be monosubstituted with an alkoxy, cyano, amino, mono- or dialkylamino, trialkylammonium-, carboxyl, sulfonic acid, acetoxy or acetamino group.

The moieties $R^2$ and/or $R^3$ preferably represent alkyl, alkoxyalkyl, cyanoalkyl, aminoalkyl, mono- or dialkylaminoalkyl, trialkylammoniumalkyl, carboxyalkyl or sulfonic acid alkyl having up to 10 carbon atoms, more preferably up to 6 carbon atoms, and especially preferred up to 4 carbon atoms in the alkyl group which may be linear or branched. Thus, $R^2$ and/or $R^3$ have the preferred meaning of methyl, ethyl, propyl, butyl, pentyl, hexyl, methoxymethyl, ethoxymethyl, 2-methoxyethyl, 2-, 3- or 4-oxapentyl, 2-, 3-, 4- or 5-oxahexyl, 2-, 3-, 4-, 5- or 6-oxaheptyl, isopropyl, 2-butyl, isobutyl, 2-methylbutyl, isopentyl, 2-methylpentyl, 3-methylpentyl, 2-oxa-3-methylbutyl, 3-oxa-4-methylbutyl, 2-methyl-3-oxapentyl, 2-methyl-3-oxahexyl, and further also heptyl, octyl, nonyl or decyl.

Further preferred are also alkyls groups which have been substituted with a cyano, carboxy- or sulfonic acid group. Thus, $R^2$ and/or $R^3$ have the preferred meaning of cyanomethyl, cyanoethyl, cyanopropyl, cyanobutyl, cyanopentyl, cyanohexyl, 2-cyanopropyl, 2-cyanobutyl, carboxylmethyl, carboxylethyl, carboxylpropyl, carboxylisopropyl, carboxylbutyl, carboxylpentyl, carboxylhexyl, carboxyl-2-methylpropyl, carboxyl-2-methylbutyl, sulfonic acid-methyl, sulfonic acid-ethyl, sulfonic acid-propyl, sulfonic acid-butyl, sulfonic acid-pentyl, sulfonic acid-hexyl, sulfonic acid-2-methylpropyl, sulfonic acid-2-methylbutyl, sulfonic acid-3-methylbutyl, sulfonic acid-2-methylpentyl, sulfonic acid-3-methylhexyl or sulfonic acid-2-ethylpentyl.

It is further preferred that the alkyl groups are monosubstituted with an amino, mono- or dialkylamino or trialkylammonium group. The alkyl groups may be same or different and may have up to 10, preferably up to 6 carbon atoms, and especially preferred up to 4 carbon atoms. Thus, they have the preferred meanings of dimethylaminoethyl, diethylaminoethyl, methylaminoethyl, methylaminopropyl, dimethylaminopropyl, ethylaminoethyl, propylaminoethyl, propylaminopropyl, dipropylaminoethyl, dipropylaminobutyl, diethylaminoethyl, trimethylammoniumethyl, trimethylammoniumpropyl, trimethylammoniumbutyl, triethylammoniumethyl, triethylammoniumpropyl, triethylammoniumethyl, aminoethyl, aminopropyl, aminobutyl or aminopentyl. Alle of these alkyl- and substituted-alkyl groups are also preferred as substituents of the phenyl group.

Likewise preferred for $R^2$ and/or $R^3$ is a sulfone sulfide having the structure —$(CH_2)_n$—$SO_2$—$(CH_2)_n$—S—$(CH_2)_n$OH with n=2, 3, 4, 5 or 6, preferably 2, 3 or 4.

Preferably, $R^2$ and/or $R^3$ also has/have the meaning(s) of a phenyl group, which preferably is mono-substituted with cyano, cyanoalkyl, amino, aminoalkyl, mono- or dialkylamino, alkyl, alkoxy, alkoxyalkyl, mono- or dialkylaminoalkyl, trialkylammonium- or trialkylammoniumalkyl, carboxy, carboxyalkyl, sulfonic acid or sulfonic acid-alkyl. The preferred meanings of these substituents correspond to those alkyl groups and substituted alkyl groups specified hereinabove as being preferred. The substituent of the phenyl group preferably is attached in the p-position.

p-Acetoxyphenyl, p-aminophenyl or p-acetaminophenyl are also preferred meanings for $R^2$ and/or $R^3$. Further preferred as moieties $R^2$ and/or $R^3$ are an alkylphenyl or a phenylalkyl group, where the specified preferred meanings are also intended to be applicable to the alkyl, substituted-alkyl or substituted-phenyl groups.

Accordingly, for example, the following substituted phenyl groups are deemed to be especially preferred: 4-cyanophenyl, 4-alkylphenyl, 4-(N,N-dimethylamino) phenyl, 4-(N,N-dialkylaminoethyl)-phenyl, 4-ethoxyphenyl, 4-ethoxyethylphenyl, 4-trialkylammoniumphenyl, 4-carboxylphenyl, 4-sulfonic acid-phenyl, phenylethyl, 4-(N-ethylamino)phenylpropyl or 4-cyanophenylethyl.

Further preferred are moieties having the formula I and/or monomers of the formula II, wherein $R^2$ and/or $R^3$ represent a cyclic or bicyclic group which may be aromatic or saturated and contains from 5 to 10 carbon atoms, in which rings one or more CH- or $CH_2$-groups will have been replaced by N or NH, N or NH and S, or N or NH and O.

Thus, $R^2$ and $R^3$ preferably also stand for a pyridine moiety, imidazolyl group, indolyl group, further preferred for a pyrrole, pyrimidine, pyrazine, quinoline or isoquinoline moiety.

$R^2$ and/or $R^3$ may also represent, for example, a thiazole, thiadiazole, morpholine, triazine, piperazine, benzothiazole, purine, pyrazole, triazole, pyrrolidine or isoxazole moiety.

Among these, the aromatic heterocyclic groups are particularly preferred.

In order to produce suitable exchangers, the groups $R^2$ and $R^3$ must be adjusted to each other in such a manner that both moieties contain either an acidic group or a basic group or one of the moieties is neutral. The artisan will not have any trouble to assign the groups accordingly and, hence, to combine suitable moieties for $R^2$ and $R^3$, depending on the function and object of the desired ion exchange.

It is preferred that one of the two moieties $R^2$ and $R^3$ is a neutral moiety.

Preferred meanings of $R^4$ include alkyl, alkoxyalkyl, cyanoalkyl, carboxyalkyl and sulfonic acid-alkyl having up to 10 carbon atoms, preferably having up to 6 carbon atoms and especially preferred having up to 4 carbon atoms in the alkyl group which may be linear or branched. Thus, $R^4$ preferably represents methyl, ethyl, propyl, butyl, hexyl, methoxymethyl, ethoxymethyl, 2-methoxyethyl, 2-, 3- or 4-oxapentyl, isopropyl, 2-butyl, isobutyl, 2-methylbutyl, isopentyl, 2-methylpentyl, 3-methylpentyl, 2-oxa-3-methylbutyl, 3-oxa-4-methylbutyl, 2-methyl-3-oxapentyl or 2-methyl-3-oxahexyl.

Further preferred are also alkyl groups substituted with a cyano, carboxy or sulfonic acid group. Thus, $R^4$ preferably represents cyanomethyl, cyanoethyl, cyanopropyl, cyanobutyl, cyanopentyl, cyanohexyl, 2-cyanopropyl, 2-cyanobutyl, carboxylmethyl, carboxylethyl, carboxylpropyl, carboxylisopropyl, carboxylbutyl, carboxylpentyl, carboxylhexyl, carboxyl-2-methylpropyl, carboxyl-2-methylbutyl, sulfonic acid-methyl, sulfonic acid-ethyl, sulfonic acid-propyl, sulfonic acid-butyl, sulfonic acid-pentyl, sulfonic acid-hexyl, sulfonic acid-2-methylpropyl, sulfonic acid-2-methylbutyl, sulfonic acid-3-methylbutyl, sulfonic acid-2-methylpentyl, sulfonic acid-3-methylhexyl or sulfonic acid-2-ethylpentyl.

All of these alkyl and substituted-alkyl groups are also preferred as substituents of the phenyl group.

Preferably, $R^4$ also has the meaning of a phenyl group, which preferably is monosubstituted with cyano, cyanoalkyl, alkyl, alkoxy, alkoxyalkyl, carboxy, carboxyalkyl, sulfonic acid or sulfonic acid-alkyl. The preferred meanings of these substituents correspond to those alkyl groups and substituted alkyl groups specified hereinabove as being preferred. The substituent of the phenyl group preferably is attached in the p-position.

$R^7$ and $R^8$ in the monomers of the formula II preferably represent H, so that R' and R" in formula I also preferably represent hydrogen.

Also preferred are separating materials wherein in formula I Y represents —OH and one of the moieties R' and R" also represents —OH. Then, a vinylene carbonate of the formula III has to be employed as the monomer, and the resulting product will have to be subsequently converted into a hydroxyl phase.

$R^7$ and $R^1$ in formula III preferably represent H. In formula I, n denotes the number of repeating units and represents from 2 to 100 and preferably from 5 to 60, with chain lengths of from 10 to 30 being preferred.

Woods, K., and Orme, Th., in the EP-A-0 239 859, describe that it is advantageous, after the virus removal or inactivation and prior to the chromatographic separation to extract the sample with oils, and preferably with soybean oil, castor oil and/or cottonseed oil.

The procedures according to the invention for the first time enable a highly pure antihemophilia factor to be prepared in high yield, which factor has a specific activity that has not been attained hitherto.

A commercially available cryoprecipitate is divided into pieces of about from 1 to 2 cm in size and is allowed to thaw at room temperature within from 3 to 4 hours. These pieces are suspended while stirred in about twice their volume of water containing 1 to 3 U/ml of heparin-sodium at temperatures between 10° C. and 25° C. The suspension is adjusted to a pH value of from at least 7.0 to 8.0 and preferably of from 7.0 to 7.1 with 0.1M acetic acid. Stirring is continued at room temperature for from 15 to 60 minutes, and preferably for 30 minutes. Then, about 108 g of a 2% aluminum hydroxide suspension are added per 1 kg of cryoprecipitate, and the mixture is stirred at room temperature for from 1 to 10 minutes, and preferably for 5 minutes. Then, the acidity is adjusted with acid, preferably 0.1M acetic acid, to a pH value of from 6.0 to 7.0 and preferably of from 6.5 to 6.6. The sample is cooled to from 18° C. to 10° C., and preferably to from 16° C. to 14° C. At this temperature, the mixture is subjected to centrifugation, for example in a Sharples AS-16 (Cepa 61) centrifuge, at a rate of 1.0 L/min. This is followed by filtration of the supernatant, through a Pall AB-1 UO1OZP filter. Virus inactivation is carried out preferably after centrifugation and filtration. A virus inactivation by means of Tween/TNBP (tri-n-butylphosphate) has proven to be particularly useful. Good result ars also obtained by using sodium cholate/TNBP. The Tween/TNBP or sodium cholate/TNBP mixture may in turn be removed, for example, by an extraction with oil.

The sample is charged onto a chromatography column containing the gel permeation material known by the trade name of EMD-TMAE-Fractogel (M) 650, which material exhibits ion exchanger activity. EMD-TMAE-Fractogel (M) 650 has already been characterized hereinabove. The column capacity preferably such that 0.5 kg of the column material per 1 kg of the cryoprecipitate are present in the column. The sample is loaded onto the column and washed with buffers. After elution of the sample with a buffer of higher ionic strength, the resulting product is diluted with a buffer having a lower salt content and, if required, is adjusted to a pH value of from 6.5 to 7.5, and preferably of from 6.9 to 7.1. Then, another filtration is carried out, preferably on nitrocellulose filters, which is followed by a sterile filtration.

Those separating buffers have proven to be particularyly advantageous, the ionic strength of which has been adjusted by using sodium chloride and/or a quaternary ammonium salt having at least one hydrocarbyl chain having vom 1 to 6 carbon atoms and bearing a hydrophilic substituent, such as choline chloride.

Thus, in the process according to the invention the column containing the above-decribed Fractogel (M) 650 is washed and equilibrated with a buffer A. Buffer A contains sodium chloride or choline at a concentration of from 50 to 200 mM, and preferably of 120 mM, and has a pH value of from 5.8 to 7.8, and preferably of from 6.5 to 7.0.

The sample is preferably applied to the column from a buffer having an osmolarity of from 200 to 600 mosm, and preferably from 380 to 520 mosm, at a pH value of from 5.8 to 7.8, and preferably of from 6.5 to 7.0. It is recommended that the capacity of the column should not exceed about 50 I.U. of factor VIII per 1 ml of gel. After the column has been loaded, it is washed with buffer A.

Then the column is washed with buffer B which also contains sodium citrate, calcium chloride, glycine, but has a higher ionic strength than the buffer A. The concentration of the quaternary ammonium salt of the above-described kind and/or of sodium chloride should be between 150 mM and 250 mM, and preferably from 180 to 200 mM, and the pH value should be between 5.8 and 7.8, and preferably about 7.0.

Elution from the column of the product is effected with a buffer C which has an ionic strength further increased over that of buffer B. The content of the quaternary ammonium salt of the above-described kind, especially choline chloride, and/or of sodium chloride should be within the range of from 200 mM and 500 mM, and preferably amount to about 400 mM, at a pH value of from 5.8 to 7.8, and preferably of about 7.0.

As the starting material, blood plasma may be employed in the place of cryoprecipitate. In this case, chromatographic processing in two steps is recommended.

By means of the process according to the invention, the recovery of factor VIII is accomplished in a higher yield and with higher product stability. It is advantageous that in the process according to the invention the so-called von-Willebrand factor is not removed, but remains in the factor VIII fractions. Thus, it is possible to use the factor VIII preparations also for patients suffering from a deficiency in von-Willebrand factor. Furtheron, factor VIII can also be employed in continuous-infusion techniques, due to the presence of the von-Willebrand factor which facilitates a natural stabilization of factor VIII.

The process is further illustrated by way of the following examples.

EXAMPLE 1

Accumulation of factor VIII from cryoprecipitate

A commercially available cryoprecipitate is divided into pieces of about from 1 to 2 cm in size and is allowed to thaw at room temperature within from 3 to 4 hours. These pieces are suspended while stirred in about twice their volume of water containing 2 U/ml of heparin-sodium at temperatures between 20° C. and 25° C. The suspension is adjusted to a pH of from 7.0 to 7.1 with 0.1M acetic acid. Stirring is continued at from 20° C. to 25° C. for 30 minutes. 108 g of a 2% aluminum hydroxide suspension are added per 1 kg of cryoprecipitate, and the mixture is stirred at room temperature for 5 minutes. Then, the pH value is adjusted with 0.1M acetic acid to from 6.5 to 6.6. The sample is cooled to from 16° C. to 14° C., subjected to centrifugation in a Sharples AS-16 (Cepa 61) centrifuge at a rate of 1.0 L/min. The supernatant is filtered through a Pall AB-1 UO1OZP filter.

EXAMPLE 2

Preparation of the chromatographic column

A column containing at least 0.5 l of ion exchanger resin per 1 kg of the cryoprecipitate is used for the separation of the extracted cryoprecipitate. The height of the column should be $\leq$ diameter. After the column has been filled with the resin, the chromatography column is first washed with 5 volumes of 0.1M sodium chloride solution. This is followed by washing with a buffer A having the following composition:

120 mM of sodium chloride, 10 mM of sodium citrate.5 $H_2O$, 120 mM of glycine, 1 mM of calcium chloride.2 $H_2O$, pH value 6.5 to 7.0, adjusted with 1M HCl.

All of the buffers must be virus-free, since the following operations are carried out with virus-free extracts of the cryoprecipitate.

EXAMPLE 3

The sample is charged to the column, and the absorption of the flow is observed at a wave length of 280 nm. The filtrate is collected and investigated for factor VIII activity, as well as the product was before undergoing the column separation. Then the column is washed with buffer A, until the absorption will again have reached its initial value. Then the column is washed with buffer B, until the absorption will again have returned to the base line.

The buffer B has the following composition:

180 to 200 mM of sodium chloride, 10 mM of sodium citrate.5 $H_2O$, 120 mM of glycine, 1 mM of calcium chloride.2 $H_2O$, pH value 6.9 to 7.0.

Elution of the product is effected with buffer C. The protein fraction appearing after the addition of buffer C is collected.

The buffer C has the following composition:

400 mM of sodium chloride, 1 mM of sodium citrate.5 $H_2O$, 120 mM of glycine, 1.0 mM of calcium chloride.2 $H_2O$, pH value 6.9 to 7.0.

After the desired product has been eluted, the column is washed with 5 volumes of buffer D, which contains a 1M sodium chloride solution.

Regeneration of the column is effected by washing same with 0.1N NaOH (3 column volumes), followed by washing the column with 0.1N hydrochloric acid (3 column volumes and washing the column with 5 column volumes of 25% alcohol in water.

EXAMPLE 4

The collected fractions are diluted with buffer E, consisting of 20 mM of sodium citrate, 80 mM of glycine, 2.5 mM of calcium chloride.2 $H_2O$, pH value 6.9 to 7.1, until they have an activity of 26 or 35 U/ml aufweisen. Then the pH-value is adjusted, if required, to from 6.9 to 7.1, which is followed by filtration through a 0.45 μm Sealklean Filter. A further sterile filtration is subsequently carried out.

EXAMPLE 5

If a human plasma is to be used as the factor VIII source, the following procedure is employed:

Fresh or deep-frozen human plasma is allowed to reach a temperature of 20° C., optionally by using a water bath. The plasma is diluted with 50% by volume of water and then filtered. The plasma filtrate is charged onto an ion exchanger column containing EMD-TMAE-Fractogel (M) 650, which column in advance had been equilibrated with a buffer having the following composition:

50 mM of sodium chloride, 10 mM of sodium citrate, 120 mM of glycine,

100 U/L of heparin, pH value 6.5 to 6.9

After the sample has been charged, the ion exchanger resin is washed several times with the washing buffer. Then the concentration of common salt is incrementally increased in that first a buffer containing 100 mM of sodium chloride is used for washing, followed by washing with a buffer with 160 mM of sodium and thereafter with a buffer containing 200 mM of sodium chloride. The fractions containing factor VIII are collected and stabilized by adding 1.0 mg/ml of human serumalbumin thereto. The resulting product is further processed in the same manner as in Examples 2 through 4, except for replacing the commercially available cryoprecipitate used therein by the column fractions obtained.

EXAMPLE 6

Comparative Experiment

In each of two runs, 0.3 kg of a cryoprecipitate obtained from an identical-plasma is processed, one procedure being in accordance with the present invention and the other one being in accordance with the process of EP 0 343 275 A1. The fractions are subjected to analysis, and the results relating to the ingredients are shown in the following Table.

Table

Comparison of chromatographic purifications of a cryoprecipitate solution by the process according to the invention (I) and by the process of EP 0 343 275 A1 (II).

| Analytical results | I | II |
|---|---|---|
| Factor VIII activity [I.U./ml] | 27 | 27 |
| VWF-AG [I.U./ml] | 66 | 23 |
| VWF-AG/Factor VIII activity | 2.4 | 0.85 |
| Fibrinogen [mg/ml] | <0.0 | 0.01 |
| Fibronectin [mg/ml] | 0.08 | 0.07 |
| IgG [mg/ml] | <0.08 | <0.08 |
| IgM [mg/ml] | <0.03 | 0.2 |
| Total Protein [mg/ml] | 0.4 | 0.3 |
| Yield Factor VIII/kg of plasma | 297 | 207 |

The workup by the process according to the invention results in 33 dispensed portions each containing 270 I.U. of factor VIII, conforming to a yield 29,700 I.U. of factor VIII/kg of cryoprecipitate or 297 I.U./kg of plasma.

The workup by the process according to EP 0 343 275 A1 results in only 23 dispensed portions each containing 270 I.U. of factor VIII, corresponding to a yield 20,700 I.U. of factor VIII/kg of cryoprecipitate or 207 I.U./kg of plasma. Therefrom ensues an advantage with respect to the yield of almost 51% over the work-up method of EP 0 343 275 A1.

Undesirable proteins such as fibrinogen and immunoglobulin M (IgM) are more efficiently removed in the process according to the invention.

We claim:

1. A process for recovering a highly pure virus-inactivated factor VIII/von Willwbrand factor complex from a sample of blood plasma or cryoprecipitate comprising subjecting the sample to an anion exchange chromatography involving the steps of:

applying the sample to a hydroxyl-group containing anion exchanger material surface-coated with covalently bonded polymers, said polymers containing repeating units which are the same or different and are represented by the formula I

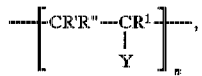

wherein $R^1$ represents H or $CH_3$

Y represents

—CN, —CHO, —OH, —$CH_2$—$NH_2$ or —$CH_2NR^2R^3$,

R' and R" each represent H or $CH_3$, while, if Y=—OH, one of R' and R" may also be —OH, X represents —OH, —$NR^2R^3$ or —$OR^4$, $R^2$ and $R^3$ each represent an alkyl, phenyl, phenylalkyl or alkylphenyl group having up to 10 carbon atoms in the alkyl moiety, which groups may be mono- or poly-substituted with alkoxy, cyano, amino, mono- or dialkylamino, trialkylammonium, carboxyl, sulfonic acid, acetoxy or acetamino moieties, a cyclic or bicyclic moiety having from 5 to 10 carbon atoms, wherein one or more CH- or $CH_2$-groups have been replaced by N or NH, N or NH and S, or N or NH and O, or a sulfone sulfide having the structure —$(CH_2)_n$—$SO_2$—$(CH_2)_n$—S—$(CH_2)_n$OH, wherein n=2–6, and one of $R^2$ and $R^3$ represents H, while $R^2$ and $R^3$ have been adjusted to each other so that both moieties either contain acidic groups or basic groups or one of the two moieties is neutral, n represents from 2 to 100, and $R_4$ represents an alkyl, phenyl, phenylalkyl or alkylphenyl group having up to 10 carbon atoms in the alkyl moiety, which groups may also be mono- or poly-substituted by alkoxy, cyano, carboxyl, sulfonic acid or acetoxy moieties;

washing and eluting the sample-applied exchanger material with buffers having, successively, increasing ionic strengths, characterized in that the ionic strength of said buffers is increasingly adjusted by a quaternary ammonium salt having at least one hydrocarbyl chain having from 1 to 6 carbon atoms and bearing a hydrophilic substituent, alone, or in combination with sodium chloride.

2. The process according to claim 1, wherein Y in formula I represents

with X=—$NR^2R^3$, wherein $R^2$ and $R^3$ each represent alkyl, alkoxyalkyl, cyanoalkyl, aminoalkyl, mono- or dialkylaminoalkyl, trialkylammoniumalkyl, carboxyalkyl, sulfonic acid-alkyl each having up to 10 carbon atoms in the alkyl moiety, phenyl which is unsubstituted or has been mono- or poly-substituted with alkyl, alkoxy, alkoxyalkyl, cyano, cyanoalkyl, aminoalkyl, amino, mono- or dialkylamino, mono- or dialkylaminoalkyl, trialkylammonium, trialkylammoniumalkyl, carboxy, carboxyalkyl, sulfonic acid, sulfonic acid-alkyl, acetoxy oder acetamino group(s) having up to 10 carbon atoms in the alkyl moiety, a cyclic or bicyclic moiety having from 5 to 10 carbon atoms, wherein one or more CH- or $CH_2$-groups have been replaced by N or NH, N or NH and S, or N or NH and O, or a sulfone sulfide having the structure —$(CH_2)_n$—$SO_2$—$(CH_2)_n$—S—$(CH_2)_n$OH, wherein n=2–6, and one of $R^2$ and $R^3$ represents H, while $R^2$ and $R^3$ have been adjusted to each other so that both moieties either contain acidic groups or basic groups or one of the two moieties is neutral.

3. The process according to claim 1 wherein the quaternary ammonium salt is choline chloride.

4. The process according to claim 1 wherein the quaternary ammonium salt, alone, or in combination with sodium chloride, has a total concentration of 0.1 to 1M.

* * * * *